United States Patent [19]

Higgins

[11] 4,323,649

[45] Apr. 6, 1982

[54] BIOTRANSFORMATIONS USING METHANE-UTILIZING BACTERIA

[75] Inventor: Irving J. Higgins, Wingham, England

[73] Assignee: Imperial Chemical Industries Limited, London, England

[21] Appl. No.: 125,660

[22] Filed: Feb. 28, 1980

[30] Foreign Application Priority Data

Mar. 9, 1979 [GB] United Kingdom .............. 08357/79

[51] Int. Cl.³ .............................................. C12P 7/40
[52] U.S. Cl. ..................................... 435/136; 435/42; 435/156; 435/189; 435/858
[58] Field of Search ................. 435/42, 136, 146, 156, 435/166, 170, 858

[56] References Cited

PUBLICATIONS

Colby et al., "The Soluble Methane Mono-oxygenase of *Methylococcus capsulatus*, Biochem. J. (1977), vol. 165, pp. 395–402.

Colby et al., Proc. Soc. Gen. Microbiology, vol. 5, p. 101 (1978).

*Primary Examiner*—R. B. Penland
*Attorney, Agent, or Firm*—Cushman, Darby & Cushman

[57] ABSTRACT

A process for the partial degradation of complex cyclicorganic compounds such as 1-phenylheptane and m-chlorotoluene using methane-utilizing microorganisms or enzyme extracts thereof containing the enzymes methane mono-oxygenase and/or a de-halogenase. The preferred microorganism is *Methylosinus trichosporium* strain OB3b (NCIB 11131).

4 Claims, No Drawings

BIOTRANSFORMATIONS USING METHANE-UTILIZING BACTERIA

This invention relates to biotransformations of organic compounds using methane-utilizing bacteria or extracts thereof.

The methane mono-exygenase of the Type I methane-utilizing micro-organism *Methylococcus capsulatus* (Bath) shows broad substrate specificity, oxidising a range of hydrocarbons and related compounds (Colby et al, 1977, Biochem. J., 165, 395). Whole organisms and cell free extracts of Type II methane-utilising micro-organism *Methylosinus trichosporium* (OB 3b) also show this ability to oxygenate a range of compounds (Colby et al., 1978, Proc Soc. Gen. Microbiol., 5, 101) and this is thought to be due to the activity of the methane mono-oxygenase of this species which appears to differ in some of its other properties from that of *Mthc. capsulatus* (Bath) (Tonge et al, 1977 Biochem. J., 161, 333: Colby et al., 1978, Biochem. J., 171, 461: Colby et al, 1978, Proc. Soc. Gen. Microbiol., 5, 101).

We have now found that methane-utilizing bacteria can also catalyse extensive partial degradation of complex organic compounds.

Accordingly the present invention provides a process for the partial degradation of a complex organic compound (as hereinafter defined) into one or more other organic compounds wherein the complex organic compound is contacted with a methane-utilizing bacterium or with an extract thereof containing a methane mono-oxygenase and/or a de-halogenase enzyme.

In this specification the term complex organic compound means a saturated or unsaturated (including aromatic) cyclic (including heterocyclic and multiple ring compounds) compound having at least one substituent, which is a halogen atom, a group containing a halogen atom and/or a substituted or unsubstituted hydrocarbon group containing at least three carbon atoms, attached to a saturated or unsaturated ring.

Suitably the complex organic compound is either (A) a mono-, di- or tri- alkyl or alkenyl benzene or (B) a di- or tri-substituted benzene in which at least one substituent is a halogen atom or a group containing a halogen atom. Preferably type (A) compounds are mono-alkyl benzenes having from 5 to 12 carbon atoms in the alkyl group, for example 1-phenylheptane which is degraded to yield benzoic and cinnamic acids and p-hydroxy-1-phenylheptane. Type (B) compounds contain e.g. alkyl or hydroxyl groups and halogen (particulary chlorine) atoms, for example m-chlorotoluene which, using washed cell suspensions, is dechlorinated and oxidised to benzyl alcohol and a hydroxy-benzyl alcohol.

The process may be carried out using whole cells (either viable or non-viable) of the bacteria or using appropriate enzyme extracts. When whole cells are used these may be flocculated using the process of UK Pat. No. 1368650. Enzyme extracts may be immobilised using the process of co-pending European Patent Application No. 79301464.8 - Publication No. 8498/80 (5 Mar. 1980).

Any suitable methane-utilizing bacteria may be used in the process including both Type I and Type II bacteria. However Type II bacteria are preferred. Such bacteria fall into the family group Methylomonadacae as described in Bergey's Manual (1974) although the classification of such bacteria is not finally decided. Suitable bacteria include strains of the genera Methylosinus, Methylocystis, Methylomonas, Methylococcus and Methylobacterium. Particularly useful strains include strains of *Methylosinus trichosporium* (e.g. the OB 3b strain), *Methylocystis parvus*, *Methylomonas albus* (e.g. the BG 8 strain), *Methylomonas methanica* (e.g. the PM strain) which are described by Whittenbury et al (J. Gen. Microbiol., 61, 1970, 205-218) and also strains of *Methylococcus capsulatus* (described in J. Bacteriol., 1966, 91, No. 5, 1929 and in "Microbial Growth on $C_1$ compounds" (1975), ed. G Terui, publ. The Soc. of Fermentation Technology, Tokyo - Article by Whittenbury et al at page 7). Suitable strains of *M. capsulatus* include the Texas strain (ATCC 19069) and the Bath strain (NCIB 11132). Other strains which can be used include strains of *Methylobacterium organophilum*.

Cultures of *Methylosinus trichosporium* strain OB 3b have been deposited at The National Collection of Industrial Bacteria (NCIB), Torrey Research Station, Aberdeen, Scotland, UK (as NCIB No. 11131) and at The Fermentation Research Institute (FRI), Japan (as FERM-P4981).

For a given substrate the products obtained may vary depending upon the system used such as enzyme extracts or whole cells. Thus when a halogen-substituted compound is treated with whole cells or with an extract containing a mono-oxygenase and a de-halogenase both oxidation and de-halogenation occur whilst with an extract containing only a de-halogenase or a mono-oxygenase then only de-halogenation or oxidation respectively occur. Other conditions affecting the products obtained include process conditions and the strain of micro-organism. Optimum conditions can be readily determined by a worker experienced in this field. When, with whole cells or extracts, it is desired to achieve both oxidation and dehalogenation over lengthy periods it is necessary to provide a co-factor acting as a source of reducing power. Suitable co-factors include methane and particularly methanol. The dehalogenase can function without a co-factor in these circumstances and hence if de-halogenation only is required no co-factor is necessary.

Before use in the process cultures of *Methylosinus trichosporium* OB 3b can be grown under batch or continuous conditions with methane as a carbon source. The cells from the cultures can be harvested during the late logarithmic phase (batch culture) or during the steady state (continuous culture) by centrifuging at 3000 g for 45 minutes. The cells are then washed twice with 20 mM sodium phosphate buffer (e.g. at pH 7.0) and, after resuspending in the same buffer, they may be stored at a low temperature, i.e. 0° C. or less, until required for use.

The above is an example of the mode of producing suitable cells of one strain. Workers skilled in the art will know how to vary these conditions in particular instances or when using other strains.

A typical transformation using cells of *Methylosinus trichosporium* strain OB 3b prepared as described above may be performed in the following manner. A washed suspension, containing 70-80 mg dry weight of cells in 20 ml of 20 mM sodium phosphate buffer (pH 7.0) is shaken in a 250 ml conical flask for 12 hrs at 30° C. The flask is sealed when containing an atmosphere of air or 50% v/v air/methane. The liquid substrates in 3 ml volumes are contained in centre wells from which they can diffuse to contact the bacterium. Products obtained may be identified by combined gas chromatography and mass spectrometry.

In a useful application of the process of the invention aqueous wastes comprising complex organic compounds (as hereinbefore defined) are treated with methane-utilizing bacteria or with extracts thereof containing a methane mono-oxygenase and/or a dehalogenase enzyme to cause partial degradation of the compounds and thereby to facilitate disposal of the wastes. This application is particularly useful where the compound is a halogen-containing compound especially a chlorine-containing compound.

The invention is illustrated by the following examples:

EXAMPLE 1

1-phenylheptane was degraded using cells of *Methylosinus trichosporium* strain OB 3b prepared as described above. A washed suspension, containing 70–80 mg dry weight of cells in 20 ml of 20 mM sodium phosphate buffer (pH 7.0) was shaken in a 250 ml conical flask for 12 hrs at 30° C. The flask was sealed when containing an atmosphere of air or 50% v/v air/methane. 3 ml of the liquid substrate was contained in a centre well from which it could diffuse to contact the bacterium. The products obtained were identified by combined gas chromatography and mass spectrometry as benzoic acid, cinnamic acid and p-hydroxy-1-phenylheptane.

EXAMPLE 2

Using the method of Example 1 m-chlorotoluene was dechlorinated and oxidised using a suspension of washed cells of *Methylosinus trichosporium* strain OB 3b prepared as described above to yield benzyl alcohol and a hydroxy benzyl alcohol. The products were identified by combined gas chromatography and mass spectrometry.

I claim:

1. A process for the partial degradation of a complex organic compound
selected from the group consisting of mono-alkyl benzenes having from 5 to 12 carbon atoms in the alkyl group and di-substituted lower alkyl benzenes having at least one halogen substituent,
into at least one other oxidized and/or dehalogenated organic compound, said process comprising the step of contacting the complex organic compound with a methane-utilizing bacterium of a genus selected from the group consisting of Methylosinus, Methylocystis, Methylomonas, Methylococcus and Methylobacterium or with an extract thereof containing a methane mono-oxygenase and/or a de-halogenase enzyme under conditions suitable for enzymatically partially degrading the complex organic compound.

2. A process according to claim 1 wherein the complex organic compound is 1-phenylheptane which is degraded to produce a mixture comprising benzoic acid, cinnamic acid and p-hydroxy-1-phenylheptane.

3. A process according to claim 1 wherein the complex organic compound is m-chlorotoluene which is degraded to produce a mixture containing benzyl alcohol and a hydroxy-benzyl alcohol.

4. A process according to claim 1 wherein the methane-utilizing bacterium is *Methylosinus trichosporium* strain NCIB No. 11131.

* * * * *